(12) United States Patent
Kacinskaite-Satkauske

(10) Patent No.: US 12,076,446 B2
(45) Date of Patent: Sep. 3, 2024

(54) MENSTRUAL TAMPON

(71) Applicant: UAB "AVODES", Kaunas (LT)

(72) Inventor: Audrone Kacinskaite-Satkauske, Kaunas (LT)

(73) Assignee: UAB "AVODES", Kaunas (LT)

( * ) Notice: Subject to any disclaimer, the term of this patent is extended or adjusted under 35 U.S.C. 154(b) by 870 days.

(21) Appl. No.: 17/132,485

(22) Filed: Dec. 23, 2020

(65) Prior Publication Data

US 2021/0121596 A1 Apr. 29, 2021

Related U.S. Application Data

(63) Continuation-in-part of application No. PCT/IB2019/055332, filed on Jun. 25, 2019.

(30) Foreign Application Priority Data

Jun. 25, 2019 (WO) .................. PCT/IB2019/055332

(51) Int. Cl.
| | | |
|---|---|---|
| *A61F 13/15* | (2006.01) |
| *A61F 13/20* | (2006.01) |
| *A61F 13/34* | (2006.01) |
| *A61F 13/551* | (2006.01) |
| *A61L 15/28* | (2006.01) |
| *A61L 15/42* | (2006.01) |

(52) U.S. Cl.
CPC .......... *A61L 15/28* (2013.01); *A61F 13/2031* (2013.01); *A61F 13/2045* (2013.01); *A61F 13/2051* (2013.01); *A61F 13/34* (2013.01); *A61F 13/55175* (2013.01); *A61L 15/425* (2013.01); *A61F 13/2074* (2013.01)

(58) Field of Classification Search
CPC ........ A61L 15/28; A61L 15/425; A61F 13/20; A61F 13/2045; A61F 13/2051; A61F 13/34; A61F 13/55175; A61F 13/2074
See application file for complete search history.

(56) References Cited

U.S. PATENT DOCUMENTS

| | | | | |
|---|---|---|---|---|
| 6,350,931 B1 * | 2/2002 | Martin | .................. | A61F 15/003 604/385.18 |
| 2002/0142693 A1 * | 10/2002 | Buzot | ................. | A61F 13/2051 442/413 |
| 2012/0165599 A1 * | 6/2012 | Ellefson | .................. | A61F 13/34 600/29 |

(Continued)

FOREIGN PATENT DOCUMENTS

| | | |
|---|---|---|
| CA | 1157437 | 11/1983 |
| DE | 2840340 A1 | 3/1979 |
| JP | S5450192 A | 4/1979 |

(Continued)

OTHER PUBLICATIONS

Office Action received in Japanese Patent Application No. 2020-573496, dispatch date Dec. 6, 2021, 7 pages.

*Primary Examiner* — Jacqueline F Stephens
(74) *Attorney, Agent, or Firm* — Hayes Soloway PC

(57) ABSTRACT

A menstrual tampon includes a sponge structure having a prewetted natural material, a special tampon form, and an outer fluid-impervious layer. The tampon also includes an applicator for easy insertion of a tampon, but can be used without an applicator, and a string or ring for convenient removal.

14 Claims, 7 Drawing Sheets

(56) References Cited

U.S. PATENT DOCUMENTS

2014/0012221 A1    1/2014  Henson
2015/0209468 A1*  7/2015  Aviles .................... C12N 1/20
                                                                                    424/447

FOREIGN PATENT DOCUMENTS

| JP | 07024312 A | 1/1995 |
| JP | 2003253524 A | 9/2003 |
| JP | 2007509656 A | 4/2007 |
| JP | 2010264131 A | 11/2010 |
| KR | 20030093293 A | 12/2003 |
| WO | 2012150546 A2 | 11/2012 |

* cited by examiner

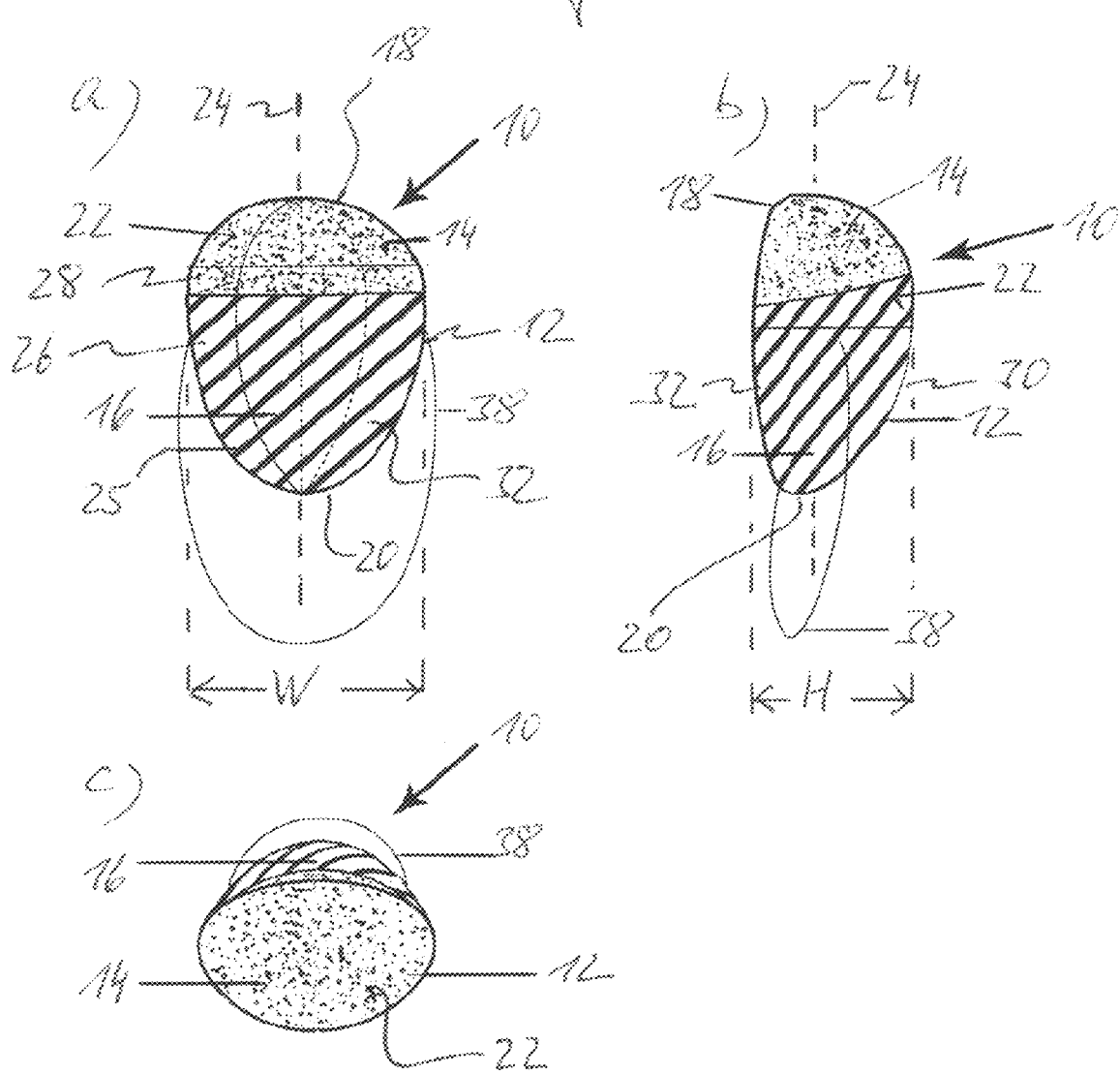

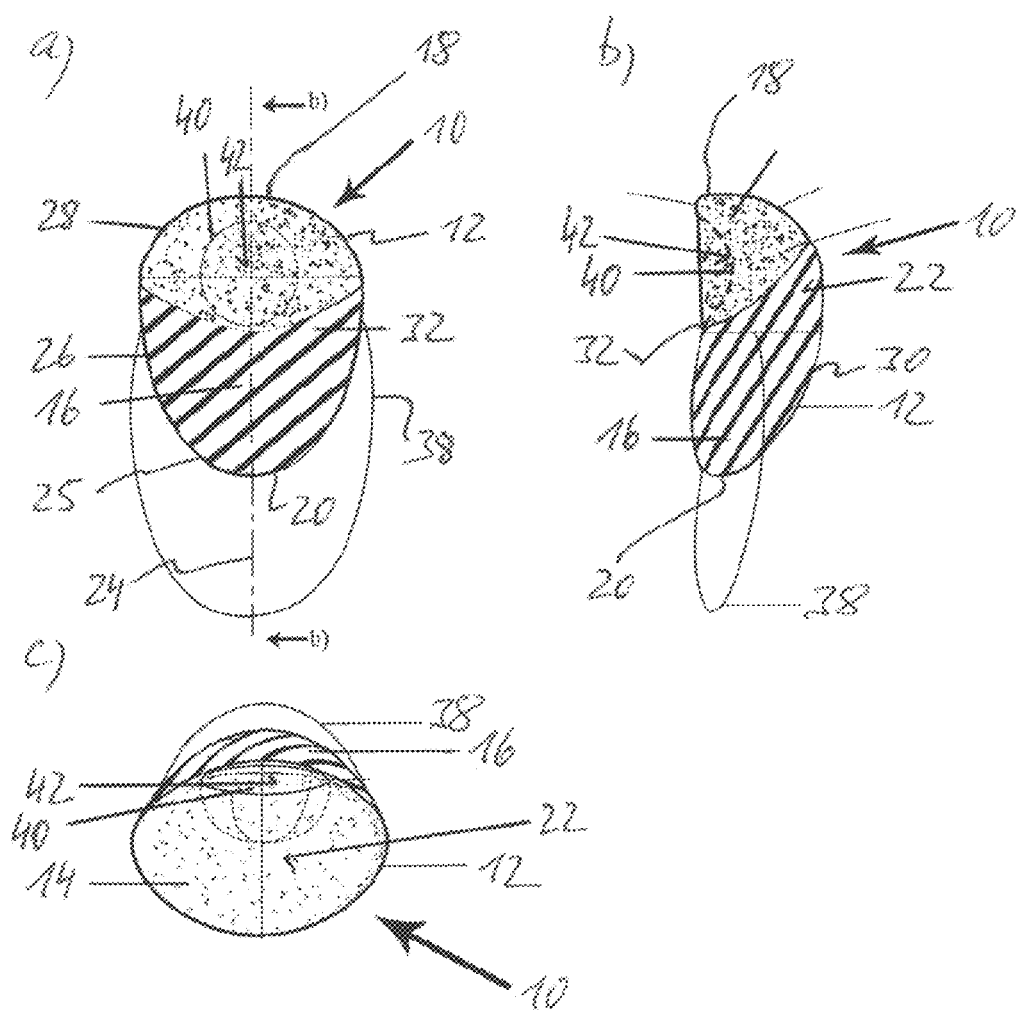

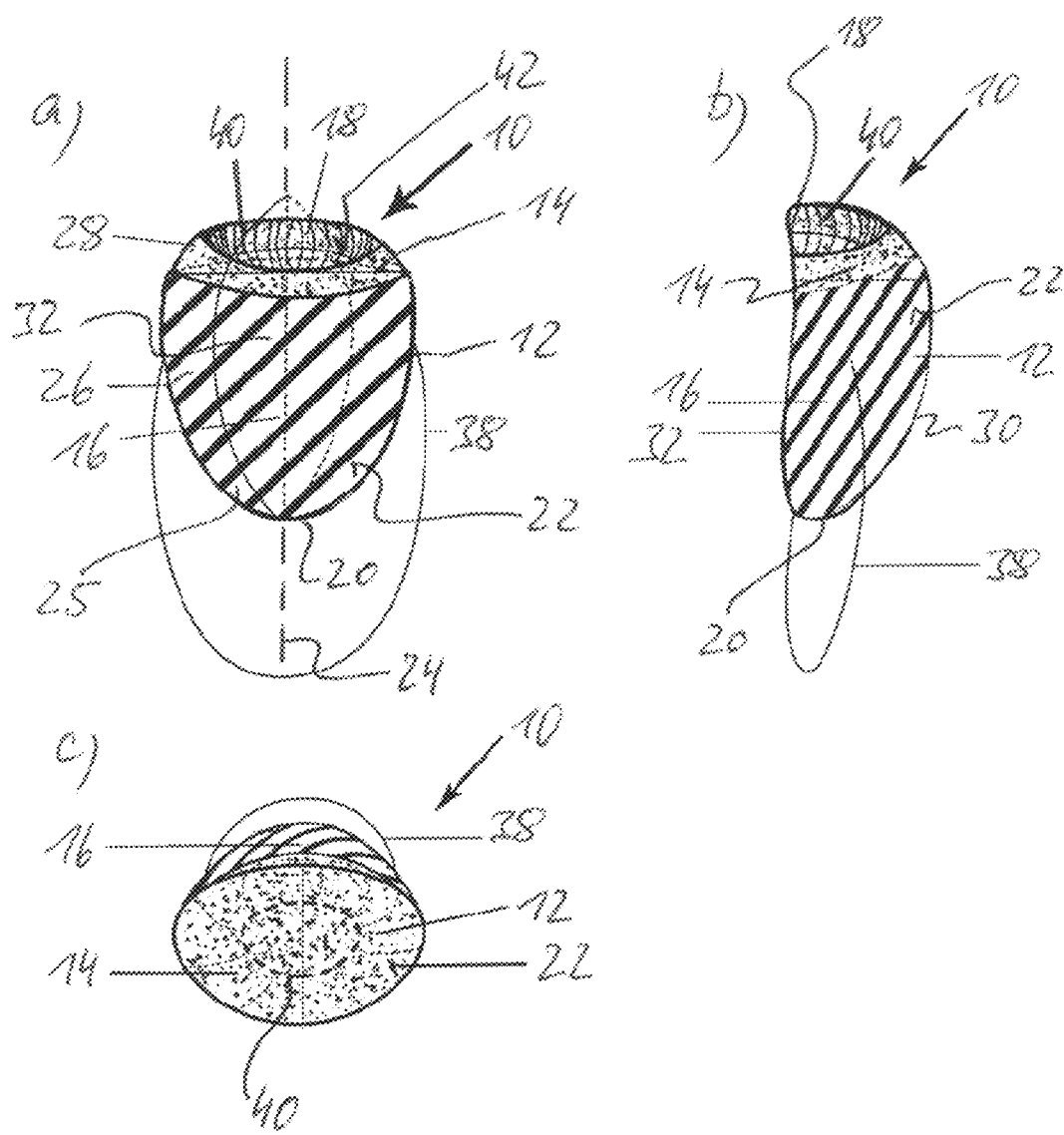

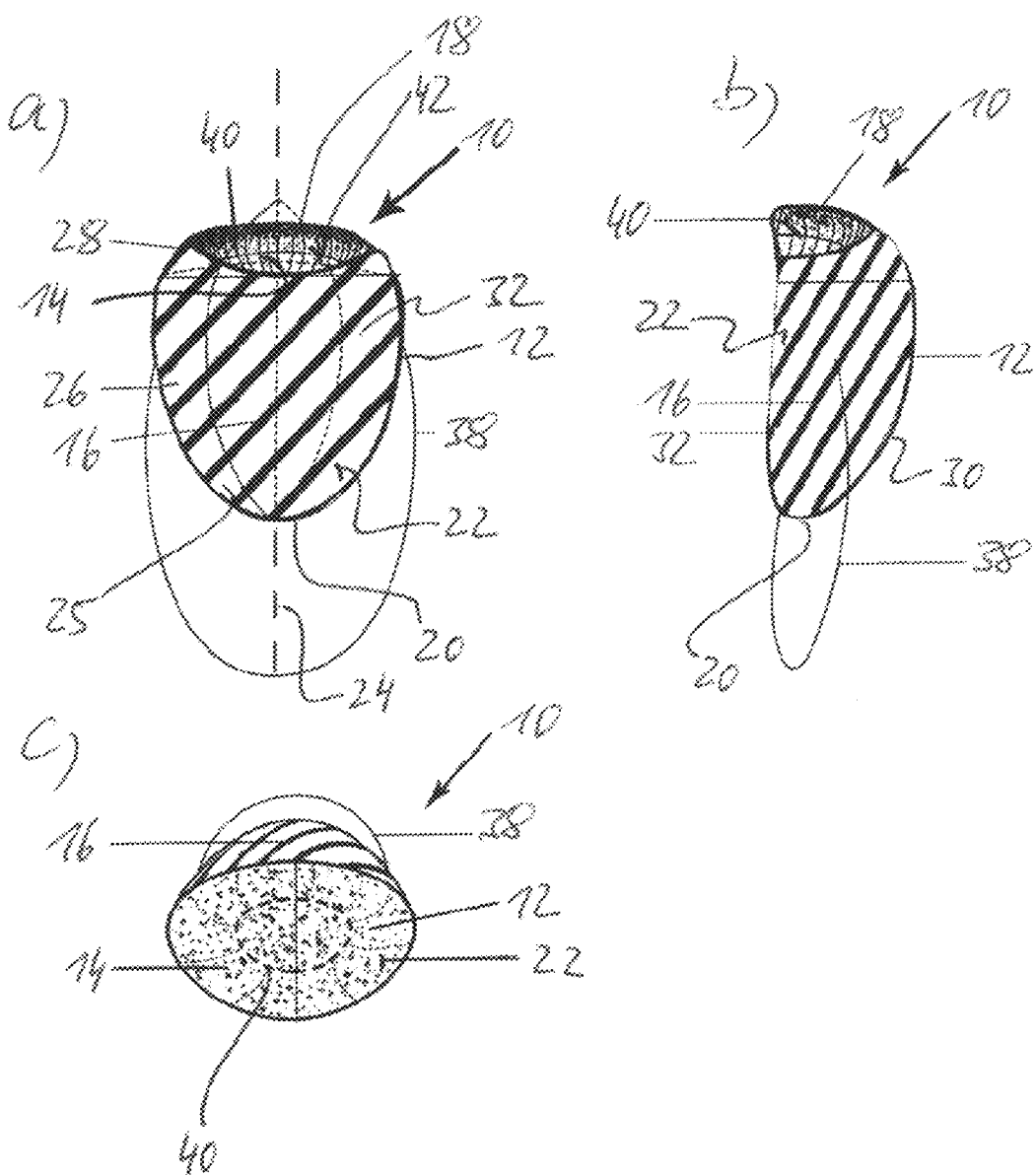

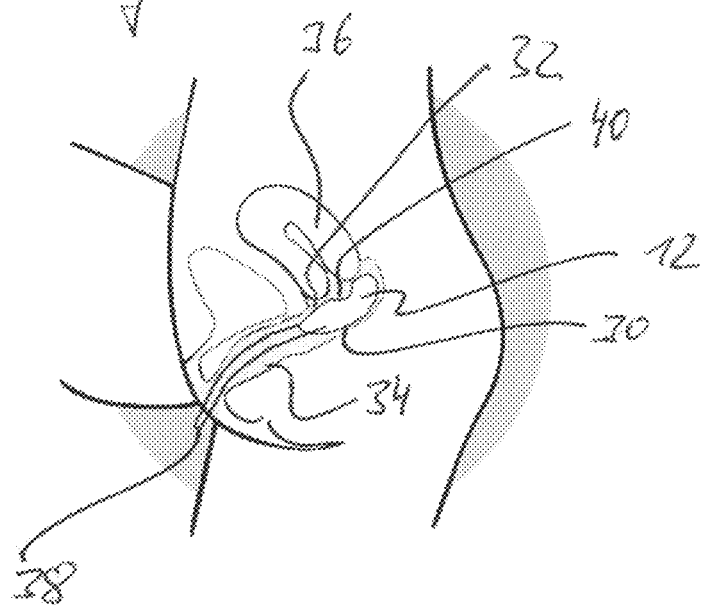
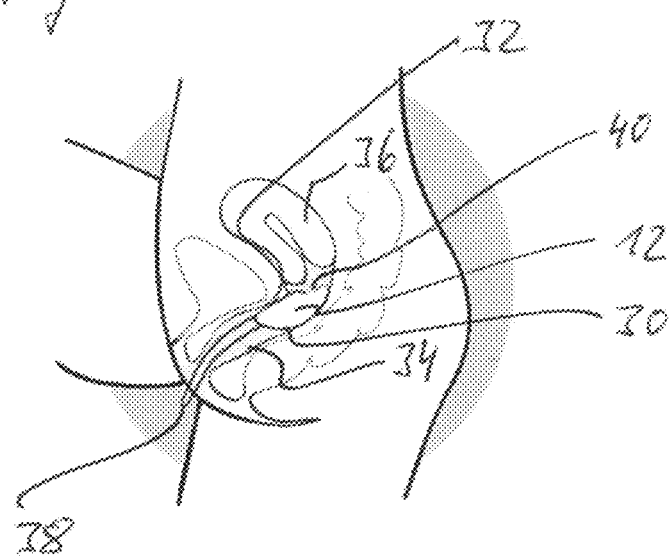

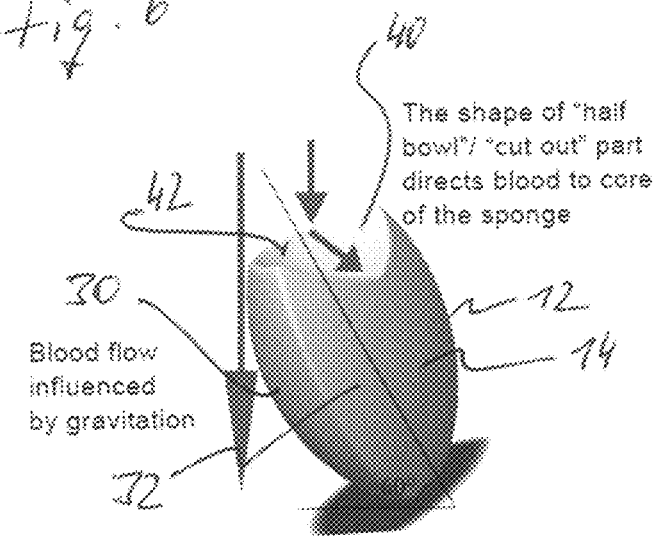
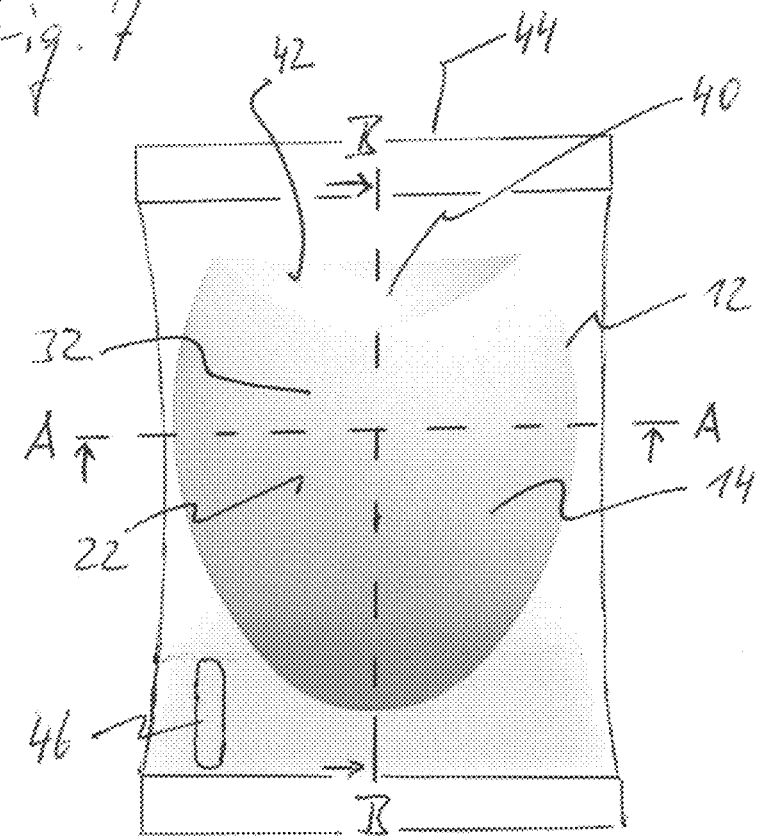

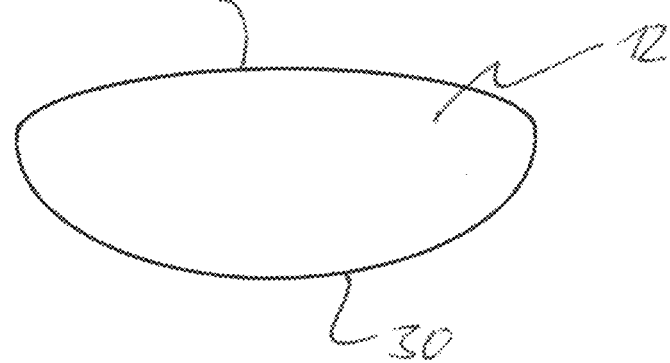
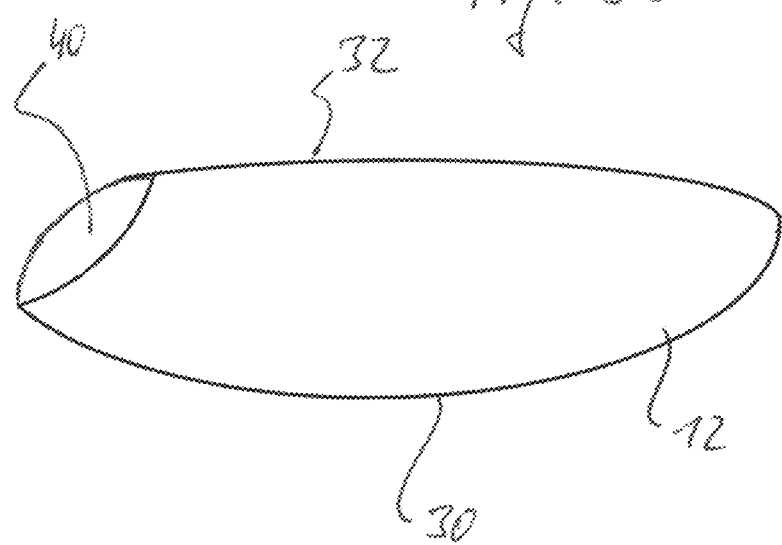

MENSTRUAL TAMPON

BACKGROUND OF THE INVENTION

1. Field of the Invention

The present invention relates generally to The invention relates to hygienic tampons, and more specifically to menstrual tampons.

2. Description of the Prior Art

Conventional hygienic tampons are made of synthetic materials, polymeric foam layer, cotton or rayon, that during production and bleaching emit dioxin, a health and environmentally hazardous pesticide (Nicole, W., 2014. A Question for Women's Health: Chemicals in Feminine Lubricants, Environmental Health Perspect 122, A70-75, https://doi.org/10.1289/ehp.122-70). Often cellulose-based tampons may have an outer layer of plastic or a plastic-coated string.

It is known that women sometimes avoid using tampons fearing for the toxic shock syndrome (TSS). Toxic shock syndrome is a rare but life-threatening disease. Up to 55% of cases are related to menstruations and 99% of those cases—to tampon usage during menstruation. TSS is caused by *Staphylococcus aureus* bacteria that is found naturally in the vaginal microflora, but that begins to multiply rapidly with changes in the vaginal pH and under other favourable conditions, for example when using tampons made from specific materials (Vostral, S L, 2011. Rely and Toxic Shock Syndrome: A Technological Health Crisis Yale J. Biol. Med. 84, 447-459), which cause vaginal colonization or infection (especially shedding material, high absorbency and chemically bleached tampons can cause the toxic shock syndrome, since particularly short, straight sharp fibres damage the vaginal walls and absorb the protective vaginal microflora). In the United Kingdom, 40 cases of this disease are diagnosed each year. Toxic shock syndrome can progress rapidly. Complications may include shock, renal failure and death.

There are cotton tampons made from pesticide-free cotton that do not pose a chemical hazard, but due to the cotton structure they absorb too much moisture from the vaginal walls (causing over-drying of the tissue) and are made up of small and sharp fibres that damage the vaginal walls and natural microflora. They leave small cotton fragments in the vagina together with old blood particles, which can also damage the vaginal pH and cause an infection.

Women exposed to contact dermatitis, lichen sclerosus—dermatitis that most often damages genital skin (statistically occurring in 108 million people worldwide, most often this disease affects women), or lichen simplex chronicus (neurodermatitis) cannot use the currently available hygiene products such as menstrual tampons or pads due to medical reasons causing pain and worsening of symptoms (Rajalakshmi, R., Thappa, D M, Jaisankar, T J, Nath, A K, 2011. Lichen simplex chronic of anogenital region: the clinico-etiological study. Indian J. Dermatol. Venereol. Leprol 77, 28-36, https://doi.org/10.4103/0378-6323.74970). The most common causes of Lichen simplex chronicus are urine and menstrual pads. As one of the major symptoms of the disease is itching, menstruation only aggravates the course of the disease. For all these diseases, clinicians advise to use natural materials for menstruation or menstrual cups if the skin is not damaged with open wounds.

With current hygiene measures, a woman may experience discomfort, infections, and some sources suggest a link to cervical cancer development. Research suggests that average levels of dioxin can cause health disorders such as embryonic development delay, birth defects, hormone disruption, and suppression of the immune cells. Due to the constant use of products that may contain dioxin, this toxin accumulates in human tissues, mainly in the fatty tissue of women and breast milk.

In order to reduce the risk of chemicals, environmental pollution and the likelihood of mechanical vaginal wall injury, natural sea sponges have been occasionally used to absorb the menstrual fluids. They are pleasant in structure, soft, and 100% natural. However, their use is not convenient due to complicated insertion/removal, a form that is not adapted to the environment that it's used in, and the need to wash it well after each use (reusable material). Also, the absorbed liquid may leak. They are particularly expensive to use as a single-use device. Because the sea sponge is a naturally occurring product, it is non-sterile and has various impurities. The US Food and Drug Administration (FDA) treats them as exceptionally risky devices that do not have the FDA approval as menstrual tampons. Data from the FDA studies shows that sand and gravel particles, bacteria, yeast, soil and even *Staphylococcus aureus* bacteria have been found in sea sponges.

WO 2017/219429 A1 discloses a synthetic menstrual sponge (which may be moist or dry) for light days of the menstrual period and may be used as a drug delivery device. The main drawbacks of this sponge are that it's synthetic (it affects the occurrence of TSS), uncomfortable insertion and removal, is only suitable for cases of mild menstruation, the form causes discomfort when using, the absorbed liquid can leak, and it presents an environment pollution problem.

EP 2 448 536 A1 describes a compressed menstrual tampon comprises an elongated rod-shaped body with a filler having an insertion end and a withdrawal end having a withdrawal string. The absorbent body with the filler expands as the fluids are absorbed and can be made from viscose, cotton, or cellulose pulp. The absorbent body with the filler may also comprise or consist of an absorbent sponge. The tampon also includes means to ease the insertion, such as an applicator that conforms to the tampon shape, from which the tampon can be expelled. However, this type of menstrual tampon is rigid, absorbs excessive amounts of moisture from the vaginal walls, is made up of small and sharp fibres that damage the vaginal walls and natural microflora, leaving small cotton fibres with old blood particles in the vagina, it can also disturb the vaginal pH and cause infections, the fluids can leak, or may cause discomfort due to uncomfortable shape.

SUMMARY OF THE INVENTION

An object of the present invention is to provide a menstrual tampon which does not have one or more of the aforementioned disadvantages. Another object of the present invention is to provide a menstrual tampon which does not harm and does not irritate the vaginal walls, does not damage the mucous membrane, reduces the likelihood of infection, facilitates insertion, prevents excessive absorption of bodily fluids, prevents leakage of menstrual fluids, is convenient during use. Yet another object of the present invention is to provide a menstrual tampon which, unlike tampons that are commonly made from absorbent fibres, comprises a sponge structure so that it can accumulate menstrual fluids in pores due to the sponge structure.

The present invention invention discloses a menstrual tampon which is introduced into the vagina to absorb menstrual fluids. One aspect of the present invention provides a menstrual tampon comprising: a tampon body having an insertion end, a withdrawal end and a body outer surface; and a removal facilitator for facilitating removal of the tampon body from a human vaginal canal. The removal facilitator is connected to the tampon body and extends from the withdrawal end of the tampon body. The tampon body comprises a sponge structure made of a glucomannan-based sponge material.

In certain embodiments, the sponge structure makes up for at least 70% or at least 80% or at least 90% or at least 95% or at least 97% or at least 99% by volume of the tampon body.

In certain embodiments, the sponge structure is exposed at least in a region of the body outer surface that is located at or near the insertion end of the tampon body. Due to the exposure of the sponge structure, the tampon body provides a surface area where menstrual fluids can be directly absorbed in the pores and/or the material of the sponge structure as the fluids arrive in and trickle down the vaginal canal.

In certain embodiments, the body outer surface has a fluid capture depression that is formed at least partially by an exposed portion of the sponge structure. The fluid capture depression can also be referred to as a fluid capture pocket. The fluid capture pocket provides in certain embodiments an absorbent surface area of at least 0.25 $cm^2$ or at least 0.5 $cm^2$ or at least 1.0 $cm^2$ or at least 2.0 $cm^2$ or at least 3.0 $cm^2$ or at least 5.0 $cm^2$ or at least 7.0 $cm^2$ or at least 10.0 $cm^2$. In these embodiments, the sponge structure is exposed inside the fluid capture depression to the outer environment of the tampon body over at least a surface area satisfying the indicated value(s). Some embodiments provide that the fluid capture depression is formed substantially entirely by an exposed portion of the sponge structure. The fluid capture depression can capture menstrual fluids as they leave the cervix uteri and enter the vaginal canal. The concavity of the fluid capture depression can ensure that menstrual fluids are guided to desired exposed areas of the sponge structure. This can enhance the absorption of the fluids in the sponge structure. The fluid capture depression may also be referred to as a surface hollow, as it defines a hollow in the outer surface of the tampon body.

In certain embodiments, the fluid capture depression is located closer to the insertion end than to the withdrawal end of the tampon body. In some embodiments, the fluid capture depression is formed at a location on the body outer surface to ensure that following placement of the tampon body at an intended vaginal position (intended for proper use) the fluid capture depression substantially faces the cervix uteri. In some embodiments, the location of the fluid capture depression on the body outer surface is chosen such that in the intended use position of the tampon body in the vagina the fluid capture depression is situated closest to the cervix uteri.

In certain embodiments, the tampon body comprises a fluid impervious layer covering the sponge structure in a partial area of the body outer surface. The fluid impervious layer may be a non-porous layer and is made in certain embodiments of a glucomannan-based material. A thickness of the fluid impervious layer may be more than 0.3 mm or more than 0.5 mm or more than 0.7 mm and may be less than 3.0 mm or less than 2.7 mm or less than 2.5 mm.

In certain embodiments, the tampon body has a length dimension in a direction from the withdrawal end to the insertion end, wherein the fluid impervious layer covers the sponge structure continuously in a region of the body outer surface that extends from the withdrawal end over at least one fourth or at least one third or at least one half of the length of the tampon body.

In another aspect, the present invention provides a menstrual tampon comprising: an absorbent tampon body having an insertion end, an opposed withdrawal ends, a longitudinal direction extending between the insertion and withdrawal ends, and a body outer surface; and a removal facilitator for facilitating removal of the tampon body from a human vaginal canal, wherein the removal facilitator is connected to the tampon body and extends from the withdrawal end of the tampon body. According to this aspect, the tampon body satisfies one or more of the following conditions (a) and (b): (a) when viewed in a cross-section orthogonal to the longitudinal direction, the tampon body has a flattened profile over at least a major part of the longitudinal extension of the tampon body; (b) the tampon body is a generally convexly shaped body having a fluid capture pocket in an upper portion of the tampon body, the fluid capture pocket having an absorbent pocket surface area of at least 1.0 $cm^2$ or at least 1.4 $cm^2$ or at least 1.8 $cm^2$.

The flattened cross-sectional profile means that the tampon body is wider than thick (high) in those longitudinal portions where the tampon body exhibits the flattened profile. The major part of the longitudinal extension of the tampon body may comprise at least 50% or at least 60% or at least 70% or at least 80% or at least 90% of the overall longitudinal extension of the tampon body. In some embodiments, the tampon body has the flattened profile over substantially the entire length of the tampon body. The flattened cross-sectional profile of the tampon body can be useful to accommodate the natural shape of the vaginal canal and make the presence of the tampon body in the vagina more comfortable for the wearer.

In certain embodiments, the flattened profile has a width that is at least 1.4 times or at least 1.6 times or at least 1.8 times or at least 2.0 times more than a height of the flattened profile. This dimensional relationship between width and height of the flattened profile applies for one or more longitudinal portions of the tampon body that comprise at least 50% or at least 60% or at least 70% or at least 80% of the overall length of the tampon body in the longitudinal direction. In some embodiments, the indicated width-height relationship applies for a all parts of a continuous portion of the tampon body that comprises at least 50% or at least 60% or at least 70% or at least 80% of the overall length of the tampon body.

In certain embodiments, the tampon body has at least one longitudinal portion for which the flattened profile has a width that is at least 1.5 cm or at least 2.0 cm or at least 2.3 cm or at least 2.7 cm or at least 3.0 cm or at least 3.3 cm. In certain embodiments, the tampon body has at least one longitudinal portion for which the flattened profile has a height of at least 1.2 cm or at least 1.4 cm or at least 1.6 cm or at least 1.8 cm or at least 2.0 cm or at least 2.4 cm or at least 2.8 cm.

The flattened profile is rotationally asymmetrical in certain embodiments.

Certain embodiments provide that the flattened profile is defined in a height direction by opposite first and second main faces of the tampon body, the first and second main faces extending between the insertion end and the withdrawal end, wherein the first main face has convexity in both the longitudinal direction and in a transverse direction, wherein the second main face has no convexity or less convexity than the first main face in the longitudinal direction and has no convexity or less convexity than the first main face in the transverse direction. Assuming that the vaginal canal of a human female generally travels upward and backward from the outer vaginal opening to the cervix, an intended orientation of the tampon body in use in the vagina may be such that the first main face is a lower face (facing substantially downward) and the second main face is an upper face (facing substantially upward). The first main face may be therefore also be referred to as a rear face of the tampon body and the second main face as a front face of the tampon body.

In certain embodiments, the tampon body has a body shape resembling a flattened egg shape having opposite first and second main faces wherein the second main face has convexity in all directions and the first main face is relatively flatter than the second main face. A relatively wider bottom end of the egg shape defines the insertion end of the tampon body, and a relatively narrower tip end of the egg shape defines the withdrawal end. The fluid capture pocket is formed in the certain embodiments at the bottom end of the egg shape.

Yet another aspect of the present invention provides a package containing a menstrual tampon, the menstrual tampon comprising a tampon body and a removal facilitator for facilitating removal of the tampon body from a human vaginal canal. The tampon body has a body outer surface and comprises a moist sponge structure which is exposed at least in a partial area of the body outer surface. The package is adapted to keep the sponge structure moist. The sponge structure is made of a glucomannan-based sponge material.

In certain embodiments, the moist sponge structure has an additional absorption capacity of at least 4 grams or at least 5 grams or at least 6 grams of menstrual fluids.

Still another aspect of the present invention provides a package containing a menstrual tampon, the menstrual tampon comprising a tampon body and a removal facilitator for facilitating removal of the tampon body from a human vaginal canal, the tampon body having a body outer surface and comprising a sponge structure which is exposed at least in a partial area of the body outer surface, wherein the sponge structure is made of a glucomannan-based sponge material, and wherein the package further contains a container holding an amount of a moisturizing liquid.

A tampon in accordance with certain embodiments of the present invention comprises a pre-moistened material of natural origin for absorption of menstrual fluids having a uniform porous sponge structure whose molecular structure prevents the occurrence of small fibres and is gentle to the vaginal walls, elastic, and shaped for an easy vaginal insertion. The special shape of the tampon and its porous structure facilitates the adaptation to the vaginal walls and ensures the impermeability of the fluids. Thanks to the shape and structure of the tampon, the liquid is absorbed where it is formed and safely retained inside the tampon. Since menstrual blood flows into and is retained in the pores of the sponge, the absorption pattern is fundamentally different from the conventional tampons that perform the function when the blood is absorbed by the tampon fabric itself. Menstrual blood accumulated in the pores of sponges is isolated from the vaginal walls, thus maintaining a healthier vaginal pH, where the healthy vaginal pH is more acidic (equal or less than 4.5) than the blood pH (about 7), thus preserving healthy microflora of vagina and reducing risk caused by pathogenic bacteria. The sponge structure allows the tampon to be compressed and deformed during use, ensuring convenience, but also function.

When the tampon is inserted, the sponge recovers its shape particularly fast due to the sponge structure, the material from which it is made of and its porosity. Softness, flexibility and special shape make it easy to adapt to individual physiology without causing discomfort. The tampon also may have an outer fluid-impervious layer that provides fluid retention in the tampon even when its deformed during use, i.e. prevents leakage of fluid as the person moves causing squeezing, bending and similar deformation of the tampon material. The tampon also may include an applicator for easy insertion and a cord, string or ring for convenient removal, but it can also be used without an applicator.

Further objects, principles and features of the present invention may become apparent from the following description which, together with the accompanying drawings, illustrate exemplary embodiments of the present invention. However, it is to be understood that these embodiments are not intended to be limiting to the scope of the invention, but instead merely serve to illustrate exemplary implementation cases.

BRIEF DESCRIPTION OF THE DRAWINGS

FIGS. 1a, b and c illustrate a menstrual tampon from the front, side and top without a hollow, respectively, according to one embodiment.

FIGS. 2a, b and c illustrate a menstrual tampon from the front, side, and top with a hollow on the side, respectively, according to another embodiment.

FIGS. 3a, b and c illustrate a menstrual tampon from the front, side and top with a hollow on top, respectively, according to another embodiment.

FIGS. 4a, b and c illustrate a menstrual tampon from the top, side and top with a hollow on top, respectively, according to another embodiment.

FIGS. 5a and 5b schematically illustrate insertion positions of menstrual tampons according to two different embodiments of the present invention in a vaginal canal.

FIG. 6 illustrates a menstrual tampon in perspective view according to yet another embodiment.

FIG. 7 illustrates an exemplary package containing the menstrual tampon of FIG. 6.

FIG. 8a schematically shows a sectional view of the menstrual tampon of FIG. 6, taken at a line A-A shown in FIG. 7.

FIG. 8b schematically shows a sectional view of the menstrual tampon of FIG. 6, taken at a line B-B shown in FIG. 7.

DETAILED DESCRIPTION OF THE INVENTION

Prior to providing a detailed description of preferred embodiments of the present invention with reference to the drawings, note that identical elements are represented by the same numerals in all drawings.

It should be understood that a number of specific details are provided to reveal a complete and understandable description of exemplary embodiments of the present invention. However, it will be apparent to a person skilled in the art that the detailing of the embodiments of the invention does not limit the implementation of the invention, which may be implemented without such specific instructions. Well-known techniques, procedures and constituents have not been described in detail so that examples of implementing the invention are not misleading. Furthermore, this description should not be considered as limiting the examples presented, but only as their implementation scheme. Any equivalent feature or modification of the features of the invention is considered to fall within the scope of the invention.

Exemplary embodiments of a menstrual tampon 10, as depicted in FIGS. 1 to 4, include an absorbent tampon body 12 comprising a solid, absorbent sponge structure 14. The material of the sponge structure 14 is a plant-derived material that can easily deform and readily reform to a non-deformed, or partially deformed state, at least in the humidified state. Such material can be produced from *Amorphophallus konjac* (Konjac plant) plant root powder by production of glucomannan and subsequently processing it by a specific method in order to obtain the sponge structure, or it can be made from other naturally occurring polysaccharides, such as starch, cellulose, chitin, and their mixtures, without limitation. The said glucomannan is a substance used in food industry, also in medicine for wound dressing which, together with lactobacteria, inhibits the growth of bacteria such as *Staphylococcus aureus* which cause the Toxic Shock Syndrome and *S. typhimurium*. The product contains no toxic chemicals and the resulting final product is chemically pure and biocompatible with the human body i.e. ensures protection of natural vaginal microflora and healthy intimate hygiene. Due to its biological origin, glucomannan-based sponge and all its additives are biodegradable and decompose naturally in nature. Glucomannan is hydrophilic and, thanks to its unique molecular structure, attracts water molecules, so the tampon walls are always moist and come in contact with the vaginal walls with a molecular barrier of liquid—protecting extremely sensitive vaginal walls.

In the embodiments of FIGS. 1a to 4c, the tampon body 12 also includes a liquid impermeable layer 16 (hatched in the drawings) which at least partially covers the sponge structure 14 to retain the moisture in the tampon body 12 until its use and prevent leakage of liquid from the tampon body 12 during its use. The liquid impermeable layer 16 covers in certain embodiments more than half, half or less than half of the outer surface of the sponge structure 14.

In certain embodiments, the liquid impermeable layer (i.e. fluid impervious layer) 16 is a non-absorbent, non-porous layer having a thickness, e.g., between 1 mm and 2 mm. It is to be understood that the indicated thickness range of the liquid impermeable layer 16 is merely exemplary and not intended to be limiting to the scope of the invention. For example, the liquid impermeable layer 16 may have in other embodiments a thickness of only a few tenths of a millimeter. The liquid impermeable layer 16 may be made of a glucomannan-based material. It can be directly formed on the sponge structure 14 after the sponge structure 14 has been produced. Other polysaccharides than glucomannan (e.g., agar, xantan gum, carrageenan or starch) can be used in alternate embodiments as a basis for the production of the liquid impermeable layer 16. It is to be understood, however, that the invention is not limited to the use of a polysaccharide material for the liquid impermeable layer 16 and that a latex or similar polymer material or a resin material can be used instead.

In embodiments which omit the liquid impermeable layer 16, the tampon body 12 may be formed entirely by the sponge structure 14. The sponge structure 14 may thus make up for up to 100% by volume of the tampon body 12. In embodiments which have the liquid impermeable layer 16, the sponge structure 14 may make up for, e.g., 90% or more by volume of the tampon body 12. The remainder of the volume of the tampon body 12 may be formed by the liquid impermeable layer 16. In certain embodiments, the sponge structure 14 makes up for at least 95% or at least 97% by volume of the tampon body 12.

The tampon body 12 has an insertion end 18, a withdrawal end 20 and a body outer surface 22. The insertion end is the leading end of the tampon body as the tampon body is shoved into a human vaginal canal, the withdrawal end is the trailing end of the tampon body during insertion of the tampon body. The body outer surface 22 is defined by the outer surface of the tampon body 12. Where the sponge structure 14 has one or more exposed portions (i.e. exposed to the outside of the tampon body 12), these exposed portions form at least part of the body outer surface 22. Where the liquid impermeable layer 16 is present and covers at least part of the sponge structure 14, the liquid impermeable layer 16 forms at least part of the body outer surface 22. The extension of the tampon body 12 from the insertion end 18 to the withdrawal end 20 defines a longitudinal extension (or direction) of the tampon body 12. The longitudinal extension is illustrated by a dashed line 24 in some of the Figures.

As seen in the longitudinal direction 24 from the withdrawal end 20 to the insertion end 18, the tampon body 12 has a lower portion 25, a central portion 26 and an upper portion 28, in that order. The tampon body has opposite main faces 30, 32 each extending between the withdrawal and insertion ends 18, 20. The main face 30 is a rear face of the tampon body 12 and the main face 32 is a front face, considering an intended, proper insertion position of the tampon body 12 in a human vagina 34, in which insertion position the main face 30 faces substantially downward and away from a uterus 36 of the wearer and the main face 32 faces substantially upward and toward the uterus 36, as shown in FIGS. 5a and 5b. In the embodiments shown in FIGS. 1a to 5b, the main face 30 has convexity in the longitudinal direction 24 over essentially the entire longitudinal length of the tampon body 12. The main face 32 is generally formed with a smaller degree of convexity in the longitudinal direction 24 than the main face 30. In some embodiments (see, e.g., FIGS. 2b, 3b, 4b, 5a, 5b), the main face 32, when viewed in the longitudinal direction 24, may be formed with substantially no curvature or with concavity in at least a part of the longitudinal length of the tampon body 12.

When viewed in cross-sectional profile (i.e. in a transverse plane), the main face 30 has convexity, with the main face 32 generally having a smaller degree of convexity than the main face 30 or no convexity at all. The situation of no convexity covers both a substantially straight extension of the main face 32 in the transverse plane or a profile of the main face 32 having one or more concavely shaped portions. Viewed in a cross-section orthogonal to the longitudinal direction 24, the tampon body 12 thus has an irregular, rotationally asymmetrical shape. This irregular cross-sectional shape of the tampon body may extend continuously over a major part of the longitudinal length of the tampon body 12, e.g., more than 50% or more than 60% or more than 70% or more than 80% or more than 90% of the length of the tampon body 12. certain embodiments, the tampon body 12 may also comprise an outer reinforcing casing (not shown in the drawing), which reinforces the structure of the tampon body 12 and helps maintain the desired shape.

Exemplary approximate sizes of the tampon body 12 are as follows:
Size 1: length 4.0-4.5 cm; width 1.5-2.0 cm; thickness ca. 1.0 cm
Size 2: length 4.5 cm; width 3.6 cm; thickness 1.9 cm
Size 3: length 5.8 cm; width 4.5 cm; thickness 2.3 cm Size 4: length 6.0 cm; width 3.9 cm; thickness 2.2 cm In all illustrated embodiments, the tampon 10 comprises a removal facilitator 38, such as a thread, ring or string. The removal facilitator 38 is coupled to the tampon body 12 and extends from the withdrawal end 20 in a manner conventionally known per se. The removal facilitator 38 may be attached at two ends to the tampon body 12 approximately in the central portion 26 or the upper portion 28 or the lower portion 25, on opposite sides of the tampon body 12 so as to form a U-shaped loop that extends from one lateral side of the tampon body 12 to the other and forms the possibility of a gap between at least the lower portion 25 of the tampon body 12 and a gripping part of the removal facilitator 38. The removal facilitator 38 can also be formed as a single element that is pierced through the tampon body 12 at any location, such as the upper, central or lower portions 28, 26, 25 of the tampon body 12.

In all illustrated embodiments, the tampon body 12 may be irregular in shape, similar to an oval, or any other sleek shape. The tampon body 12 may be generally wider near its insertion end 18 then near its withdrawal end 20. The mentioned flattened profile, according to which the width of the tampon body 12 (designated W in FIG. 1a) is larger than its height, or thickness (designated H in FIG. 1b) over at least a major part of the longitudinal length of the tampon body 12, serves to reproduce the natural biological vaginal canal form (https://i.pinimg.com/originals/d9/d1/3b/d9d13b90a7d2c5ba6e5314f2c8b3258f.jpg) to create a comfortable experience for the user. This is related to the fact that the use of solid form devices that create pressure to the front and back of the vagina (where many nerve endings are centred) generates additional pain or discomfort for the user. As can be seen from FIGS. 1a, 2a, 3a, 4a, the upper portion 28 is generally formed with a larger width than the lower portion 25. When inserted in the vagina, the tampon body 12 is located with its upper portion 28 closer to the origin of the menstrual fluids than with its lower portion 25 (cf. FIGS. 5a, 5b). The greater width of the upper portion 28 can thus enhance the absorption of the menstrual fluids in the sponge structure 14, whereas the lower portion 28 can efficiently retain the accumulated fluids in spite of its reduced width whilst ensuring high wearing comfort.

In the embodiments of FIGS. 2a to 5b, the tampon body 12 is formed with a hollow 40 exhibiting a generally concavely shaped absorption surface 42 at which the sponge structure 14 is exposed to the outside of the tampon body 12. If present, the liquid impermeable layer 16 does not cover the sponge structure 14 at the absorption surface 42. The hollow 40 may also be referred to as a fluid capture depression or pocket. The surface area of the absorption surface 42 is in certain embodiments at least 1.5 cm$^2$ or at least 2.0 cm$^2$. The hollow 40 may be concavely shaped in all directions, resembling, e.g., a bowl shape or the like.

In certain embodiments of the invention, the liquid impermeable layer 16 may cover the entire body outer surface 22 of the tampon body 12 up to the perimetrical edge of said hollow 40. In other embodiments of the invention, the liquid impermeable layer 16 may wrap the sponge structure 14 only up to a distance from the perimetrical edge of the hollow 40, so that the sponge structure 14 remains uncoated by the liquid impermeable layer 16 (i.e. exposed to the outside of the tampon body 12) not only within the area of the hollow 40 but also outside the hollow 40 in the region between the liquid impermeable layer 16 and the perimetrical edge of the hollow 40.

The hollow 40 is designed for cervix and easier fluid accumulation, and for faster fluid uptake to prevent blood stagnation at the cervix. The surface 42 comprises a portion of the material of the sponge structure 14 of the tampon body 12 and is generally concave in shape, such as in the form of a scoop, a hollow half-sphere, an oval, or any other form. Although the absorption surface 42 is said to be generally concavely shaped, it is to be understood that one or more sub-portions of the absorption surface 42 forming a part of the entire area of the absorption surface 42 may nevertheless have a plane or even convex shape. In other words, the absorption surface 42, although in general forming a concave depression or pocket, may be comprised of concave and non-concave surface portions. The hollow 40 may be formed on the main face 32 at a longitudinal position closer to the insertion end 18 than to the withdrawal end 20 (as shown exemplarily in FIGS. 2a-c and FIGS. 5a, 5b), or may be formed in the region of the insertion end 18 (as shown exemplarily in FIGS. 3a-c and 4a-c).

The tampon body 12 comprises at least a non-deformed state when it is fully expanded, a deformed state when it is compressed to occupy the smallest possible volume, and a partially deformed state in which the tampon body 12 fills the entire vaginal cavity by partially deforming the vaginal cavity walls at the contact site. In this way, the volume of fluids absorbed by the tampon body 12 is increased, while ensuring convenient vaginal adaptation. Reversible deformations of the tampon body 12 ensure that the adaptation to the vagina will take place continuously, while the user is both at rest and during movement. When the forces from the vaginal walls stop working on the tampon body 12, the deformed tampon body 12 recovers its original or partially original shape.

As can be seen from FIGS. 6, 7 and 8b, the absorption surface 42 defined by the hollow 40 has a concavely curved shape both in the width direction and the height direction of the tampon body 12 (the width and height, or thickness, dimensions are in a plane perpendicular to the longitudinal direction 24). On the side of the main face 32, the hollow 40 forms a deeper neck than on the side of the main face 30. The hollow 40 thus cuts out a relatively larger portion from the main face 32 than from the main face 30.

In certain embodiments, the tampon body 12 substantially maintains its shape and volume in a non-deformed (i.e. quiescent) state over a broad range of levels of humidification of the material of the sponge structure. It can be envisaged at least for some embodiments that in order to be able to store the tampon 10 for extended periods of time without degradation, even when packaged in a hermetic manner in a package, the material of the sponge structure 14 should rather be be relatively dryer than moister. Certain embodiments therefore include in package a capsule or other suitable container (e.g., a sachet) together with the tampon 10, the capsule or container containing a predetermined amount of water or another liquid substance to be used for moisturizing the tampon body 12 before use.

The sponge material of the tampon body 12 is humidified with water and/or other materials of liquid form. The humidifying liquid may or may not contain an impregnant. The humidifying liquid moisturizes the entire sponge material of the tampon body 12 so that it switches from the natural solid state to a soft state. Such moisturised sponge-based tampon does not dry the mucosa, but at the same time absorbs excess moisture, facilitates the insertion and removal of the tampon body 12 without damaging the particularly thin vaginal skin, since it has a soft and mild structure. A variety of substances which have a positive effect on vaginal microflora can be used as an impregnant including various medications and plant extracts to relieve and/or reduce menstrual pain or for other purposes. It is possible to use anti-candidiasis extracts, preventive/prophylactic extracts, bleeding reduction extracts, and lactobacteria. According to scientific studies, the glucomannan substance together with *Lactobacillus* inhibits the growth of bacteria such as *Staphylococcus aureus* (which cause the Toxic Shock Syndrome) and *S. typhimurium*. At the same time, women who have problems with chronic candidiasis, whose exacerbations occur before and after menstruation, would benefit from a sponge impregnated with drugs or plant extracts as preventive measures to feel comfortable and fight the disease.

Impregnation of the sponge material of the tampon body 12 with medication is a safer way to treat diseases than an oral drug intake because it protects the liver and digestive system. Due to the thin vaginal mucosa, drugs are able to reach target areas much easier. And the material from which the sponge structure 14 is made improves the release and absorption of the drug. Impregnants can perform an additional therapeutic or preventive function such as:

antiseptic—to prevent bacterial growth, anaphylactic shock, bacterial disease,
antispasmodic—e.g. impregnation with natural plant extracts,
probiotic—to maintain mucosal microflora,
contraceptive,
prophylactic—impregnation with vitamins, plant extracts, etc.,
therapeutic—impregnation with medication and other substances according to the therapist's recommendations.

Embodiments of the present invention also comprise a waterproof package 44 (FIG. 7) for said tampon 10. The package 44 is designed as a pouch in the example case shown in FIG. 7 and is configured to retain sterility and moisture of the body 12 of the tampon 10. It is to be understood that many different configurations of the pouch are conceivable and likewise many other designs of the waterproof package 44 than a pouch are conceivable, so long as the package 44 can retain a moist and sterile environment for the tampon 10. The tampon body 12 of the embodiment shown in FIGS. 6 and 7 has only the sponge structure 14, but no liquid impermeable layer 16. Also included in the package 44 is a schematically depicted capsule 46 containing an amount of, e.g., water which that the user can use to moisturize the tampon body 12 prior to its insertion into a human vagina.

Although many features and advantages have been described above, along with the structural details and features of the invention, the description is provided as an exemplary embodiment of the invention. Changes may be made to the details, in particular in the form, size and arrangement of the materials, without departing from the principles of the invention, in accordance with the most widely understood terms used in the claims.

What is claimed is:

1. A menstrual tampon comprising:
a tampon body having an insertion end, a withdrawal end, a body outer surface, and a longitudinal direction extending between the insertion and withdrawal ends; and
a removal facilitator for facilitating removal of the tampon body from a human vaginal canal, the removal facilitator connected to the tampon body and extending from the withdrawal end of the tampon body,
wherein the tampon body comprises a sponge structure made of a glucomannan-based sponge material,
wherein the body outer surface has a fluid capture depression formed at least partially by an exposed portion of the sponge structure, wherein the fluid capture depression is located closer to the insertion end than to the withdrawal end of the tampon body, and wherein the fluid capture depression is concave in shape, and
wherein the tampon body has a flattened profile over at least a major part of the longitudinal direction of the tampon body when viewed in a cross-section orthogonal to the longitudinal direction.

2. The menstrual tampon of claim 1, wherein the sponge structure makes up for at least 70% by volume of the tampon body.

3. The menstrual tampon of claim 1, wherein the sponge structure is exposed at least in a region of the body outer surface that is located at or near the insertion end of the tampon body.

4. The menstrual tampon of claim 1, wherein the tampon body comprises a fluid impervious layer covering the sponge structure in a partial area of the body outer surface.

5. The menstrual tampon of claim 4, wherein the fluid impervious layer is made of a non-porous, glucomannan-based material.

6. The menstrual tampon of claim 5, wherein the tampon body has a length dimension in a direction from the withdrawal end to the insertion end, wherein the fluid impervious layer covers the sponge structure continuously in a region of the body outer surface that extends from the withdrawal end over at least one fourth of the length of the tampon body.

7. The menstrual tampon of claim 1, wherein the tampon body has one or more longitudinal portions for which the flattened profile has a width that is at least 1.4 times more than a height of the flattened profile, the one or more longitudinal portions comprising at least 50% of the overall length of the tampon body.

8. The menstrual tampon of claim 1, wherein the tampon body has at least one longitudinal portion for which the flattened profile has a width that is at least 1.5 cm.

9. The menstrual tampon of claim 1, wherein the tampon body has at least one longitudinal portion for which the flattened profile has a height of at least 1.2 cm.

10. The menstrual tampon of claim 1, wherein the flattened profile is rotationally asymmetrical.

11. The menstrual tampon of claim 1, wherein the flattened profile is defined in a height direction by opposite first and second main faces of the tampon body, the first and second main faces extending between the insertion end and the withdrawal end, wherein the first main face has convexity in both the longitudinal direction and in a transverse direction, wherein the second main face has less convexity than the first main face in the longitudinal direction and has less convexity than the first main face in the transverse direction.

12. The menstrual tampon of claim 1, wherein the tampon body has a body shape resembling a flattened egg shape having opposite first and second main faces wherein the second main face has convexity in all directions and the first main face is generally relatively flatter than the second main face, the egg shape having a relatively wider bottom end than the withdrawal end and a relatively narrower tip end than the insertion end,
wherein the bottom end of the egg shape defines the insertion end of the tampon body and the tip end of the egg shape defines the withdrawal end, and
wherein the fluid capture depression is formed at the bottom end of the egg shape.

13. The menstrual tampon of claim 1, wherein the fluid capture pocket has an absorbent pocket surface area of at least 0.25 cm².

14. A package containing a menstrual tampon, the menstrual tampon comprising:
- a tampon body having an insertion end, a withdrawal end, a body outer surface, and a longitudinal direction extending between the insertion and withdrawal ends, and
- a removal facilitator for facilitating removal of the tampon body from a human vaginal canal,
- the tampon body having a body outer surface and comprising a sponge structure which is exposed at least in a partial area of the body outer surface,
- wherein the sponge structure is made of a glucomannan-based sponge material,
- wherein the body outer surface has a fluid capture depression formed at least partially by an exposed portion of the sponge structure, wherein the fluid capture depression is located closer to the insertion end than to the withdrawal end of the tampon body, and wherein the fluid capture depression is concave in shape,
- wherein the tampon body has a flattened profile over at least a major part of the longitudinal direction of the tampon body when viewed in a cross-section orthogonal to the longitudinal direction, and
- wherein the package further contains a container holding an amount of a moisturizing liquid for moisturizing the tampon body before use.

\* \* \* \* \*